United States Patent [19]

d'Hinterland et al.

[11] Patent Number: 4,460,575

[45] Date of Patent: Jul. 17, 1984

[54] VACCINAL COMPLEX CONTAINING A SPECIFIC ANTIGEN AND VACCINE CONTAINING IT

[75] Inventors: Lucien D. d'Hinterland; Gerard Normier; Anne-Marie Pinel; Jacques Durand, all of Castres, France

[73] Assignee: Pierre Fabre S.A., France

[21] Appl. No.: 236,534

[22] Filed: Feb. 20, 1981

[30] Foreign Application Priority Data

Feb. 20, 1980 [FR] France ............................. 80 03707

[51] Int. Cl.$^3$ .................... A61K 39/02; A61K 39/09; C07C 103/52; C07H 21/02
[52] U.S. Cl. ........................................ 424/92; 424/88; 424/180; 424/177; 536/27; 260/112 R
[58] Field of Search .................... 424/92, 88; 536/22, 536/27, 28, 29; 260/112 R

[56] References Cited

U.S. PATENT DOCUMENTS

| | | | |
|---|---|---|---|
| 3,725,545 | 4/1973 | Maes | 424/88 |
| 3,952,097 | 4/1976 | Levy | 536/22 |
| 4,285,930 | 8/1981 | Likhite | 424/92 |

OTHER PUBLICATIONS

Chemical Abstracts, vol. 87, p. 376, Abst. No. 11603w, 1977.

*Primary Examiner*—Blondel Hazel
*Attorney, Agent, or Firm*—Maky, Renner, Otto & Boisselle

[57] ABSTRACT

The present invention relates to a vaccinal complex containing a specific antigen. This is a vaccinal complex characterized in that it is composed of bacterial ribosomal RNA or fragments of bacterial ribosomal RNA on which are coupled from 1 to 5% by weight of a specific antigen of bacterial serotype. This complex may be used as a vaccine.

14 Claims, No Drawings

VACCINAL COMPLEX CONTAINING A SPECIFIC ANTIGEN AND VACCINE CONTAINING IT

This invention relates to specific bacterial antigen complexes coupled to ribosomal RNA or ribosomal RNA fragments originating from the same bacteria or from different bacteria, to a process for the preparation thereof and to vaccines containing them.

It is known for a large number of bacteria that their vaccinal ability is connected to the presence of specific antigens.

These are almost always surface antigens present in walls, membranes, capsules or released in soluble form into the culture medium. Their nature is essentially polysaccharide, polypeptide or glycoprotein. These antigens are well known and methods for the preparation thereof have been widely described in the literature.

Direct use of these specific serotype antigens as vaccines, attractive though it is, is not always straightforward. The antigenic ability of these substances is often moderate, which leads to the administration of high doses in order to obtain significant protection. However, at such doses, these antigens are sometimes still toxic. For example, in the case of capsular polysaccharides, these are generally involved in the pathogenicity of bacteria and the use of high vaccinal doses presents serious disadvantages.

It has been observed that ribosomal RNA or fragments of the same RNA may advantageously be used as active conveyors of these specific antigens with which they form a particularly immunogenic complex at very low doses, due, it seems, to a spatial structure which may be directly used by the immuno-competent cells of the organism.

It is for this reason that the present invention relates to a vaccinal complex characterised in that it is composed of bacterial ribosomal RNA or fragments of bacterial ribosomal RNA on which are coupled from 1 to 5% by weight of a specific antigen of bacterial serotype.

According to the invention, the ribosomal RNA and the specific antigen may originate from the same bacterial strains or from different strains.

The term "coupling" is generally understood to mean at least one bond between the two types of molecule, a bond which is preferably covalent formed by a reaction of the different functions of the molecules which are present, but which may be of a different nature.

The ribosomal RNA which may be used may be extracted in particular from ribosomes of the following strains:

*Streptococcus pneumoniae,*
*Streptococcus pyogenes,*
*Staphylococcus aureus,*
*Klebsiella pneumoniae,*
*Serratia marcescens,*
*Escherichia coli,*
*Salmonella typhimurium,*
*Corynebacterium (parvum, acnes, granulosum),*
*Mycobacterium (tuberculosis, Smegmatis).*

However, it has been observed that ribosomal RNA could advantageously be replaced by fragments of RNA of a lower molecular weight, obtained in particular by hydrolysis from this same ribosomal RNA.

This hydrolysis may notably be carried out by conventional chemical or enzymatic methods using ribonucleases. The molecular weight of the fragments obtained is between $3 \times 10^4$ and $2 \times 10^5$ daltons and molecular weights of from 30,000 to 50,000 are preferably used.

The following should be mentioned among the specific antigens which may be used:
capsular polysaccharides notably of:
*Klebsiella pneumoniae*
*Streptococcus pneumoniae*
*Hemophilus influenzae*
*Escherichia coli;*
membrane lipopolysaccharides of gram negative bacteria, notably:
*Klebsiella pneumoniae*
*Serratia marcescens*
*Escherichia coli*
*Neisseria meningitidis*
*Salmonella typhimurium;*
specific membrane proteins, notably:
*Escherichia coli*
*Serratia marcescens*
*Salmonella typhimurium*
*Streptococcus pyogenes;*
teichoic and lipoteichoic acids, notably of:
*Streptococci*
*Staphylococci*
*Lactobacillae*

A large number of processes have been described for the preparation of these specific antigens according to their chemical nature and to their localization on the surface of the bacterium, or in the culture medium, these descriptions being made in particular in the documents mentioned which are included in the following as references.

A-Capsular polysaccharides:

polysaccharides which are essential constituents of the capsule of certain bacteria are generally released in abundance into the culture medium. Thus, their extraction is possible either from the biomass, or directly from the culture.

Capsular polysaccharides generally have a simple chemical structure, formed from the repetition of one molecule composed of from 2 to 4 sugars, and this structure is characteristic of the bacterial type which is considered. These are thus specific antigens and the antibodies which they produce are generally protectors. However, they are thus almost always involved in the pathogenicity of bacteria and their direct administration in a vaccinal dose, which is often large (from 50 to 200 μg), presents serious disadvantages. The use of doses which are considerably reduced in the form of a complex with RNA thus allows the risks to be eliminated while retaining a very strong immunostimulant power.

The following articles concerning these capsular polysaccharides relate to processes for obtaining them and the immunizing activities for some bacterial strains where the role of the capsular polysaccharides has been clearly established.

*Klebsiella pneumoniae*

C. ERBING, L. KENNE, B. LINBERG, J. LONNGREN (1976)— Structural studies of the capsular polysaccharide of *Klebsiella pneumoniae* type I (Carbohydr. Res, 50 (1976), 115–120)

W. NIMMICH (1968)—Zur isolierung und qualitativen bausteinanalyse der K. angigen vol Klebsiellen (Z. med. MIKROBID. u. IMMUNOL, 154, 117, 131).

C. RICHARD (1973)—Etude antigenique et biochimique de 500 souches de Klebsiella (Ann. Biol. Clin. (1973), 3, 295-303).

The capsular polysaccharide of *Klebsiella pneumoniae* type I is by way of example a polymer of the following trisaccharide unit:

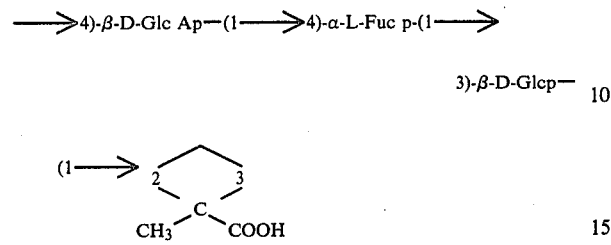

Glc = glucose, Fuc = fucose,
Glc Ap. = glucuronic acid

*Streptococcus pneumoniae:*

The study of 83 different capsular types has been described by KAUFFMANN. F. and LUND E (1954) (Int. Bull. bact.Nomencl, 4, 125-128).

The immunostimulant ability of these pneumococcal capsular antigens was observed as early as 1920 by Felton and was studied in depth by Felton and Ottinger (J.of Bacteriology (1942), 43, 94–105)

Colin M. MacLeod M.D. and al. -Prevention of pneumonoccal *pneumoniae* by immunization with specific capsular polysaccharides (J.Exp.Med. (1945) 82,445–465).

The presence of these specific soluble antigens in the culture medium has already been indicated by: DOCHEZ, A. R. and O. T. AVERY. The elaboration of specific soluble substance by pneumococcus during growth (1917) (J.Exp. Med. 26: 477–493).

There are numerous methods for preparation of these capsular polysaccharides and they have been the subject of a large number of publications. The following should be mentioned:

WEST PHAL and LUDERITZ (Z. Naturf. (1952), 7B, 148) which are the basis of all the methods based on the use of phenol, GLAUDEMANS C. P. J. and H. P. TREFFERS—An improved preparation of the capsular polysaccharide from

*Diplococcus pneumoniae* (Carbohydr. Res. (1967), 4, 181-184).

The following should also be mentioned by way of example of known chemical structures of these capsular polysaccharides:

Capsular polysaccharide of *Streptococcus pneumoniae* type 2:

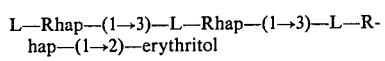

Capsular polysaccharide of *Streptococcus pneumoniae* type 5.

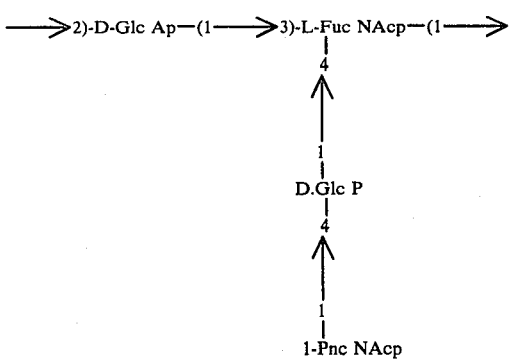

(L. Pnc. NAcp=N-acetyl—L—pneumosamine=2-acetamido—2,6—dideoxy—L. tolosyl).

Capsular polysaccharide of *Streptococcus pneumoniae* type 8.

→4)—D—Glc
A—β—(1→4)—D—Glc—β—(1→4)—D—Gl-
c—(1→4)—D—Gal—(1→

Capsular polysaccharide of *Streptococcus pneumoniae* type 14.

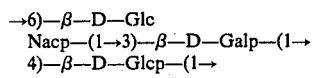

*Hemophilus influenzae*

The protector antigen of *Hemophilus influenzae* is also a capsular polysaccharide of the polyribosephosphate type, whose exact formula has not yet been determined. The preparation, immunogenicity and characterisation thereof are described in the following publications:

P. ANDERSON et al. (1972). Immunization of humans with polyribosephosphate, the capsular antigen of *Hemophilus influenzae* type b (J. of Clin. Invest. vol. 51 (1972), 39–44)

P. ANDERSON et al (1977). Isolation of the capsular polysaccharide from supernatant of *Hemophilus influenzae* type b (infect. and Immun. (1977) 15 (2), 472–477)

*Escherichia coli*

As for the above germs, the specific antigens are, partly at least, capsular polysaccharides.

LUDERITZ et al (1968)—Somatic and capsular antigens of gram negative bacteria (Compr. Biochem. 26 A: 105–228).

Their protecting ability is, however, less well established than for the preceding germs.

B-Membrane Lipopolysaccharides (LPS)

Gram negative bacteria have all the lipopolysaccharides whose general structure is composed of the following portions:

Lipid A—KDO—polysaccharide core—Antigen O

The O antigen which is positioned at the free end of the LPS is a specific polysaccharide which is strongly antigenic. However, the antibodies obtained do not always have an advantageous protecting ability and, on the other hand, the lipid portion (Lipid A) of the LPS is mostly responsible for the toxic properties of the bacterium. Therefore, direct use of such antigens can scarcely be envisaged. On the other hand, an association of RNA—purified O antigen is very advantageous.

The following should be mentioned from the bacterial species of which the LPS have been more particularly studied:

*Klebsiella pneumoniae*
*Serratia marcescens*
*Escherichia coli*
*Neisseria meningitidis*
*Salmonella typhimurium*

A few bibliographic references are also mentioned:

C. ERBING et al (1977)—Structural studies on the Klebsiella LPS (Carbohydr. Res, 56, 377–381)

G. B. CASTOR et al. (1971)—Characteristics of a highly purified pyrogenic LPS of *Klebsiella pneumoniae* (J. of Pharm. Sci, 60 (10), 1578–1580)

K. FUKUSHI (1964) Extraction and purification of endotoxin from Enterobacteriaceae: A comparison of selected methods and sources. (J. of Bacteriol. 87 (2), 391–400)

GUADALUPE A. LIMJUCO. Studies on the chemical composition of LPS from *Neisseria meningitidis* Group B. (J. of Gen. Microbiol. (1978, 104, 187–191)

G. A. ADAMS (1967)—Extraction of LPS from Gram—negative bacteria with DMSO (Canad. J. Biochem., 45, p.422–426)

K. G. JOHNSON (1976)—Improved techniques for the preparation of bacterial LPS (Canad. J. Microbiol. (22), 29–34)

Y. B. KIM et al (1967)—Biologically active endotoxins from *Salmonella mutans* (J. of. bacteriol. 94, (5), 1320–1326)

C-Specific membrane proteins

For numerous bacteria, proteins which are functionally very important are positioned on the membrane surface.

Some of these proteins are very useful specific antigens producing the formation of vaccinal antibodies.

The following should be mentioned, for example:

*Escherichia coli:*

STIRM S. F. et al (1967)—Episome—carried surface antigen K88 of *Escherichia coli* (J. Bacteriol 93 (2): 731–739)

SALLY, J. BETZ et al (1977)—Chemical and biological properties of a protein-rich fraction of bacterial LPS (J. of Immunol. 119 (4) 1475–1481)

*Serratia marcescens:*

W. WOBER (1971). Studies on the protein moiety of endotoxin from gram—negative bacteria—characterisation of the protein—moieting isolated by acetic acid hydrolysis of endotoxin of *Serratia marcescens.*

*Salmonella typhimurium:*

NORA KUUSI et al. (1979). Immunization with major outer membrane proteins in experimental salmonellosis of mice (Infact. and Immun. (1979) 25 (3), 857–862.

BARBER, C. et al (1972). The protective role of proteins from *S. typhimurium* in infection of mice with their natural pathogen (Rev. Immunol 36: 77–81)

DELORD G. (1979). Etude d'un antigene vaccinant contenu dans le surnageant de culture de *Salmonella typhimurium* Souche M-206. These medecine Lyon No. 428 (1979).

G. W. GOODMAN (2979)—Characterization of the chemical and physical properties of a novel B. Lymphocyte activator—Endotoxin protein (Infect. and Immun. (1979), 24 (3), 685–696)

*Streptococcus pyogenes:*

M. K. WITTNER (1977)—Homologous and Heterologous protection of mice with group A Streptococcal M protein vaccine (Infect. and Immun. (1977), 15, (1), 104–108)

D-Teichoic and lipoteichoic acids

Among the gam positive bacteria, teichoic and lipoteichoic acids are roughly the equivalent of LPS among the gram negatives. These teichoic acids are generally polyribitolphosphate or polyglycerolphosphate. They are specific antigens often having an advantageous vaccinal ability.

They have been studied in particular in: Streptococci (pyogenes, feacalis, pneumoniae) Staphylococci (aureau, epidermidis . . . ) Lactobacillae.

M. M. BURGER. (1966) Teichoic acids: antigenic determinants, chain separation, and their location in the cell wall (Microbiology (56) p. 910–917) K. W. KNOW (1973) Immunological properties of teichoic acids (Bacteriol. Reviews, 37 (21, 215–257) GLENN A. MILLER (1976) Effects of a Streptococcal Lipoteichoic acid on Host Response in Mice (Infect. and Immun. (1976) 13, (5), 1408–1417) A. J. WICKEN et al (1975) Lipoteichoic acids: a new class of bacterial antigens (Science: 187, 1161–1167).

The description in which all the articles mentioned above are incorporated herein by reference shows how the specific bacterial antigens are varied in their structure, their distribution and their properties. Thus, for each bacterial type, it is possible at present to isolate and to purify by known processes one or more specific protector antigens of a certain immunizing potential. As has been stated, most of these antigens often have undesirable toxic effects in the vaccinal dose.

The formation of a complex of very low quantities of these antigens with RNA or fragments of ribosomal RNA, in an administration of doses which are completely non-toxic, allows a high degree of specific protection to be obtained and thus considerably widens the possibilities of use.

The complete ribosomal RNA or the fragments thereof may be prepared by known processes.

One example of preparation of ribosomal RNA will be given, as this is a semi-industrial or industrial preparation of ribosomal RNA.

This process substantially comprises the preparation of bacterial ribosomes by fractional precipitation from ground bacteria, solubilization of ribosomal proteins by hot SDS, precipitation of the RNA which is then treated with PRONASE in order to eliminate the residual proteins, and re-purification of the RNA which is obtained by ion exchange chromatography.

The use of RNA fragments, by reducing the molecular weight of the ribosomal RNA, substantially improves its capacity for increasing the immunizing ability of the specific antigens. Numerous conventional methods, described in the literature, enable this result to be obtained.

However, it is preferred to use an enzymatic method based on the action of pancreatic ribonuclease which has the advantage of not damaging the double-chain portions of ribosomal RNA.

This method comprises incubating the solution of RNA obtained with 5 μg per ml of pancreatic ribonuclease for two hours at 37° C.

The RNA is then concentrated and purified by chromatography on DEAE cellulose as before. The fractions containing RNA are recovered by precipitation with ethanol.

A purification which is complementary but not indispensable may be obtained by selecting the fragments included between molecular weights of $5.10^4$ and $2.10^5$ daltons, either by molecular seive chromatography on Sephadex G200, or by ultrafiltration on a Diaflo uM 300 membrane.

The following articles describe other characteristics of the enzymatic degradation of the ribosomal RNA.

EHRESMANN, G. (1972) Biochimie 54: 901
KAGAWA, H. (1972) J. Biochem 72: 827
SANTER, M. (1973) J. Bact. 116: 1304
NOMURA (1974)—Ribosomes—Ed. Cold Spring Harbor Laboratory.

The RNA preparations thus obtained may be controlled particularly by the following methods.

Determination of RNA:
Three methods are used:
(1) Direct spectrophotometric determination at 256 nm compared to a standard commercial preparation.
(2) Determination of phosphorous, based on the fact that pure ribosomal RNA contains 8.2% of phosphorous (FISKE and SUBBAROW—J. Biol Chem (1926), 66,375).
(3) HPLC chromatography on an ion exchanger column after hydrolysis for the qualitative and quantitative control of the composition in purine and pyrimidine bases and the investigation of the thymine characteristic of DNA.

Investigation of DNA:
By HPLC chromatography as previously indicated and by a colour reaction with diphenylamine (BURTON K.—Biochem. J. (1956), 62, 315–322).

Investigation of proteins:
By Lowry's method (J. Biol. Chem (1951), 193, 265–275)

Investigation of hexoses:
By colorimetric determination on anthrone according to SCOTT T. A. (Analyt. Chem (1953), 25, 1956–1961).

Investigation of Hexosamines:
According to ELSON L. A. (Biochem.J. (1933), 1824–1828).

Investigation of lipopolysaccharides:
By the carbocyanine method of JANDA J. and WORK. E. (FEBS LETTERS (1971), 16, (4), 343–345). The limulus test is also used.

Determination of the molecular weight of the preparations
(1) For non-hydrolysed RNA, by molecular sieve chromatography on Biogel A 1.5 m and by density gradient ultracentrifugation.
(2) For RNA fragments, by molecular sieve chromatography on Sephadex G200 and by electrophoresis on a gradient of acrylamide gels.

Average analytical results
The determination of the molecular weights by the different methods which have been indicated produces the following results:
(1) For non-hydrolysed RNA, the two known molecules 16S and 23S are recovered with neighbouring respective molecular weights of $5.10^5$ and $1.10^6$ daltons.
(2) For RNA fragments, their average molecular weight is between $5.10^4$ and $2.10^5$ daltons.

The physico-chemical composition of the two types of preparation is practically the same: They contain at least 95% of RNA, less than 0.25% of DNA, less than 3% of proteins, less than 1% of hexoses, less than 0.1% of hexosamines and less than 0.0001% of LPS.

With the varied nature of the specific bacterial antigens, numerous processes may be used for their coupling on RNA chains.

Two large groups of antigens must be distinguished in a more general manner:
peptide antigens,
polysaccharide antigens Peptide antigens
Numerous techniques of chemical coupling allow the formation of covalent bonds between the amine groups of nucleic bases and carboxylic groups or the amine functions of terminal amino acids of peptide antigens. These techniques use, for example, reagents such as glutaraldehyde and carbodiimides.

The use in particular of carbodiimides of the general structure RN=C=NR allows the production of an amide bond between the amine of one of the bases of RNA and the carboxyl of an amino acid. According to the following reaction:

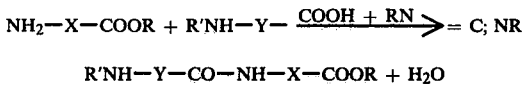

$$R'NH-Y-CO-NH-X-COOR + H_2O$$

The carbodiimide may be, for example: 1-ethyl-3-(3-dimethylaminopropyl) carbodiimide hydrochloride (EDC).

The operating conditions may be as follows:
Prepare an aqueous solution of RNA with 5 mg of RNA per ml, adjust the pH to 4.5, then add 2 mg/ml of carbodiimide to this solution. Add a solution of the peptide antigen at the same pH in the required proportions to this preparation.

The mixture is stirred for one night at ambient temperature.

The complex is precipitated by the addition of 2 volumes of cold ethanol in the presence of $CH_3COONa$ 0.2M, and is then washed with 70% alcohol containing $CH_3COONa$ 0.2M.

The complex is then dissolved in a suitable buffer, is sterilised by filtration on a $0.2\mu$ membrane and is lyophilised.

In addition to this chemical method, RNA peptide complexes may also be obtained by ultraviolet irradiation of a solution containing the RNA and the peptide. Under these conditions, covalent bonds are also obtained. The wave length used should be from 223 to 290 nm.

Polysaccharide antigens
The ribosomal RNA have a great affinity for polysaccharide structures. This property may be exploited to produce polysaccharide antigen RNA complexes.

The secondary and tertiary structures of RNA which is greatly folded mask a large portion of coupling sites. This structure, after elimination of the ribosomal proteins is maintained by the action of some divalent cations, such as magnesium.

Thus, one process comprises complexing the magnesium ion using a chelating agent, contacting the RNA which is thus unfolded with the specific antigen, then adding magnesium ions in order to obtain a complex according to the invention.

A more detailed operating method will be described in the following examples.

In the present description, the term "complex" is understood to mean a molecule having one unit which may be characterised by the following methods.

One of the methods which best allows the complexes prepared thus to be characterised is ultracentrifugation in a density gradient.

The complex solution to be analysed is introduced on sucrose gradients of from 5 to 20% formed in the tubes of an SW rotor of 14 ml, and the same procedure is carried out on other tubes for a control of RNA by itself and a control of antigen by itself.

After the bands have been stabilized on the gradient (isopicnic centrifugation) (the conditions of speed and duration of centrifugation are adapted for each case as a function of the relative molecular weights of RNA and the antigen), the tubes are collected and the gradients are eluted by means of a pump and a 35% sucrose solution.

The eluate is fractioned on a fraction collector and the optical density of each fraction is measured at 260 nm. The optical density curves at 260 nm and the curves of the index of refraction are traced on a graph. In this manner, it is possible to visualize the divergence in equilibrium density between the control RNA and the RNA which is increased in weight by the antigen.

Moreover, the fraction containing the coupled RNA is recovered and dialysed exhaustively in order to eliminate the sucrose of the gradient. (The corresponding zone of the antigen control tube is treated under the same conditions to verify that the equilibration zone of the control antigen is different).

After dialysis, a physico-chemical analysis is carried out which allows a quantatitive and qualitative measurement of the quantity of antigen bonded to the RNA.

Two other methods may also be used for characterising these complexes:

1. Molecular sieve chromatography

The complex is chromatographed on Sephadex of appropriate porosity giving elution volumes which are different for the RNA and the control antigen. The zone having an absorption at 260 nm is recovered and analysed as before. In addition thereto, the modification of the elution volume with respect to the control RNA characterises the increase in the molecular weight of the complex.

2. Electrophoresis on a polyacrylamide gel in gradients

Gradients of acrylamide of from 4 to 30% are produced by a conventional method on plates, and the control RNA, control antigen and the corresponding complex are then deposited. After one night of migration, electrophoresis is stopped and examined. The migration distances are then directly proportional to the molecular weight of the substances and a migration distance corresponding to a molecular weight which is higher than that of the control RNA is observed for the complex.

The present invention also relates to vaccines containing at least one complex such as has been previously described as an active principle.

The vaccines according to this invention may be prepared by any known process, in particular in the form of an aqueous solution, the complexes according to the invention being soluble in water.

It is evidently possible to use other supports or additives which are compatible with use in medicine.

These vaccines may also be administered by any method which substantially depends on the action investigated and on the condition of the patient: thus, the vaccines may be presented in aerosol form or in an injectable form, in particular by a subcutaneous method.

The daily doses and the frequency thereof also greatly depend on the illness to be prevented and on the condition of the patient, but if an overdose often does not provide any additional advantage, it does not present any risk, bearing in mind the very low toxicity of these vaccines.

Some examples of vaccines comprising specific antigens complexed with ribosomal RNA or fragments of ribosomal RNA are provided in the following in an illustrative and non-restricting manner.

EXAMPLE 1

A capsular antigen RNA complex of *Hemophilus influenzae* comprising the following:
ribosomal RNA of *Klebsiella pneumoniae*: 10 μg
capsular polysaccharide of *Hemophilus influenzae* b: 0.5 μg

EXAMPLE 2

Pneumococcic vaccine composed of the following complexes:
*Streptococcus pneumoniae* type I: 5 μg of RNA and 0.2 μg of capsular PS
*Streptococcus pneumoniae* type II: 5 μg of RNA and 0.2 μg of capsular PS
*Streptococcus pneumoniae* type III: 5 μg of RNA and 0.2 μg of capsular PS

EXAMPLE 3

Bronchal vaccine:
*Klebsiella pneumoniae* type I: 5 μg of RNA and 0.2 μg of capsular PS
*Streptococcus pneumoniae* type I: 5 μg of RNA and 0.2 μg of capsular PS
*Streptococcus pyogenes* AR type 12: 5 μg of RNA and 0.2 μg of teichoic acid
*Hemophilus influenzae* type a: 5 μg of RNA and 0.2 μg of capsular PS

EXAMPLE 4

Intestinal vaccine:
*Salmonella typhimurium* . . . 3 μg of RNA and 0.1 μg of membrane proteins
*Escherichia coli* . . . 3 μg of RNA and 0.1 μg of K proteins
*Shigella dysenteriae* . . . 3 μg of RNA and 0.1 μg of O antigen
*Staphylococcus aureus* . . . 3 μg of RNA and 0.1 μg of teichoic acid In order to state more precisely certain characteristics and advantages of the present invention, the following Examples give a detailed description of the preparation of the composition according to Example 2.

EXAMPLE 5

Separation of the capsules and of the cellular contents

The bacterial biomass of *Streptococcus pneumoniae* I which is used for the preparation of ribosomal RNA and the capsular PS is obtained by a conventional industrial fermentation process. The only characteristic of the fermentations intended for the preparation of the ribosomal RNA is in the centrifugation of the cultures when they are in the full phase of exponential growth and at low temperature, in order to retain a maximum activity of ribosomal synthesis in the cells.

The bacterial concentrate is washed by resuspending in physiological serum and centrifugation. The biomass is subjected to a bacteriological quality control, and is then stored frozen at low temperature.

In order to obtain capsular polysaccharides, the washed cells are dispersed in a tris-HCl buffer 0.01M, pH 7, containing NaCl 0.10M and $MgCl_2$ 0.01M.

The temperature of the suspension is brought to 40° and the capsules are separated by homogenising for a few minutes in a warring blendor at this temperature.

After cooling, the decapsulated cells are separated by centrifugation for 30 minutes at 30,000 g and 4° C.

The residue is separated for the preparation of the ribosomes and the ribosomal RNA. The supernatent containing the capsules is recovered; the treatment thereof will be described in the example.

In order to recover the intracellular contents, the residue is re-introduced in suspension in tris-HCl buffer, pH 7.2, containing $MgCl_2$ and NaCl, then the suspension is subjected to cellular disintegration in a DYNO-MILL apparatus with micro glass balls, under refridgeration.

EXAMPLE 6

Preparation of the ribosomal fraction

The uncrushed cells and the cellular debris are eliminated by two successive centrifugations at 10,000, then at 30,000 g at +4° C.

The clear supernatant obtained is treated for one hour at 37° C. with 5 µg/ml of DNase, and is then acidified to pH 5. The protein precipitate formed at this pH is eliminated by centrifugation at 30,000 g and +4° C.

The ribosomes are precipitated from the supernatant by acidification to pH 4 and are recovered by centrifugation at 10,000 g and +4° C.

The non-ribosomal proteins which are absorbed are thus eliminated by washing the ribosomes for 30 minutes at 25° C. in a 0.25% SDS solution (sodium dodecyl sulphate) in tris-HCl buffer, pH 7.5, containing $MgCl_2$ and NaCl.

The washed ribosomes are precipitated from this solution by the addition of 0.7 volumes of cold ethyl alcohol. The precipitate of ribosomes is recovered by centrifugation, and is then taken up into tris-HCl buffer, pH 7.2 containing NaCl.

The solution is clarified by centrifugation at 30,000 g and the supernatant containing the ribosomes is retained for the preparation of RNA.

EXAMPLE 7

Preparation of ribosomal RNA

The largest portion of the ribosomal proteins is eliminated from RNA by treatment with hot SDS. Some SDS is added to the suspension of the previous ribosomes in order to obtain a final concentration of 1%. The solution is then brought rapidly to 80° C. and is maintained for 5 minutes at this temperature with vigorous stirring. After rapid cooling, the RNA is precipitated by acidification to pH 4 using dilute HCl; under these conditions, 5 S RNA is not precipitated, only 16 S and 23 S RNA are precipitated. The RNA precipitate is recovered by centrifugation, is then washed with a 70% ethanol solution containing 0.2M sodium acetate at pH 7.8, in order to eliminate the residual SDS. The RNA which is thus washed and converted into the sodium salt is taken up in tris-HCl buffer, pH 7.8, and containing NaCl.

At this stage, from 5 to 10% of proteins may still contaminate the RNA. They are eliminated by treatment with pronase for one hour at 37° C.

The RNA is precipitated from this solution by slowly adding half a volume of a 5% aqueous Cetavlon solution (cetyl trimethyl ammonium bromide) and is immediately recovered by centrifugation.

The precipitate is then washed several times by dispersion and centrifugation in a 70% ethanol solution containing 0.2M sodium acetate at pH 7.8, which eliminates the residual Cetavlon.

The RNA residue is taken up in tris-HCl buffer, 0.05M, pH 7.2, and is then subjected to a final purification by ion exchange chromatography on a DEAE cellulose column. The RNA which is retained on this column is eluted after washing by a gradient of NaCl (0→0.5M) in the same buffer. The fraction containing purified RNA is recovered, and is then precipitated by adding two volumes of cold ethanol. The RNA is recovered by centrifugation and is taken up in a minimum volume of tris- HCl buffer, 0.01M, pH 7.5.

EXAMPLE 8

The supernatant containing the capsules obtained in Example 5 is treated in the following manner.

The capsular polysaccharides are initially precipitated from some supernatant by slowly adding an aqueous 2% cetyl pyridinium chloride solution, until the end of flocculation. After leaving for an hour at 4° C., the polysaccharide precipitate is recovered by centrifugation and the supernatant is removed.

The precipitated complex of polysaccharide and cetyl-pyridinium chloride is dissociated in 2M sodium chloride; under these conditions, the polysaccharide passes into solution while the cetyl pyridinium chloride is eliminated by centrifugation, and the supernatant is retained.

Three volumes of cold ethyl alcohol are added to the supernatant in order to precipitate the polysaccharide which is recovered by centrifugation after leaving for one hour at 4° C.

The precipitated polysaccharide is washed by dispersion in a water-ethanol mixture (30:70 v/v) containing $CH_3COONa$ 0.1M for 30 minutes at ambient temperature. The washing solution is removed by centrifugation and the deposit is taken up in an aqueous 0.1M solution of $CH_3COONa$.

In order to eliminate the proteins which are still able to contaminate the preparation at this stage, an extraction process is carried out for ten minutes at 65° C. with one volume of 90% phenol in sodium acetate 1M. After vigorous stirring for ten minutes at 65° C., the mixture is rapidly cooled in an ice bath and the two phases are separated by centrifugation for 5 minutes at 10,000 g and 0° C. The upper aqueous phase is carefully removed. Three volumes of cold ethyl alcohol are added to the aqueous phase and the polysaccharide is left in precipitation for 1 hour at 4° C.

The precipitate is recovered by centrifugation and is then dispersed in a water-ethanol mixture (30:70 v/v), containing $CH_3COONa$ 0.1M for 30 minutes at ambient temperature. The washed precipitate is recovered by centrifugation and is taken up in distilled water, then sterilized by filtration on a 0.22µ membrane and lyophilised.

EXAMPLE 9

Preparation of the complex

A 0.001M solution of ethylene diamine-tetraacetic acid (EDTA) is added to an aqueous solution of 5 mg of RNA/ml, prepared by the process in Example 7. The EDTA forms a complex with the magnesium ions which are then eliminated by dialysis.

The RNA structure is thus "unfolded", unmasking a maximum number of coupling sites. The polysaccharide antigen obtained in Example 8 is then dissolved at 0.2 mg/ml in the RNA solution and the mixture is stirred for one night at 4° C. After this period of stirring, some magnesium chloride is then added to the solution in order to obtain a final molarity of 0.01M and stirring is continued for two hours.

The complex is then precipitated in the presence of 0.2M $CH_3COONa$ by adding two volumes of cold ethanol.

The precipitate is washed with 70% ethanol containing 0.2M $CH_3COONa$, then taken up in a suitable buffer, sterilized by filtration on a $0.2\mu$ membrane and lyophilized.

In the same manner, the complexes corresponding to *S. pneumoniae* type II and *S. pneumoniae* type III are prepared.

EXAMPLE 10

A study of the protection of mice by formulation No. 2, against an attack by the virulent strain of Streptococcus pneumoniae type I

Animals used mice Balb/c

Formula No. 2

Streptococcus pneumoniae type I: 5 $\mu$g of RNA+0.2 $\mu$g of PS

Streptococcus pneumoniae type II: 5 $\mu$g of RNA+0.2 $\mu$g of PS

Streptococcus pneumoniae type III: 5 $\mu$g of RNA+0.2 $\mu$g of PS

Method

A—20 mice treated with 1.25 $\mu$g of mixture in 15 days, by subcutaneous method.

A'—20 control mice treated twice with 0.2 ml of saline in 15 days by subcutaneous manner.

B—20 mice treated twice with 0.6 $\mu$g of the mixture in 8 days, by subcutaneous method.

B'—20 control mice, treated twice with 0.2 ml of saline in 8 days by subcutaneous method.

Exposure to the virulent strain of *Streptococcus pneumoniae* type I took place on the sixth day after the last treatment.

Results

Group of mice A/A'

1. Exposure to 50 bacteria (*Streptococcus pneumoniae* I) by intraperitoneal method.

→Protection++very significant, 20 days after exposure group A—20 surviving animals
group A' control—12 surviving animals 2. Exposure to 5 bacteria (*Streptococcus pneumoniae* I) by intraperitoneal method.

→Protection++very significant, 20 days after exposure (group A—20 surviving animals)
(group A' control—12 surviving animals)

3. Exposure to 1 bacterium (*Streptococcus pneumoniae* I) by intraperitoneal method.

→No infection in the animals which were treated or vaccinated.

Group of mice B/B'

1. Exposure to 100 bacteria (*Streptococcus pneumoniae* I) by intraperitoneal method.

→Protection++very significant, 2 days after exposure (group B—20 surviving animals)
(group B' control—no surviving animals)

2. Exposure to 10 bacteria (*Streptococcus pneumoniae* I) by intraperitoneal method.

→Protection++very significant, 2 days after exposure (group B—20 surviving animals)
(group B' control—no surviving animals.)

For the two exposures, all the treated animals were surviving 20 days after the administration of virulent germs, whereas the control animals were all dead 2 days afterwards.

| | INVESTIGATION BY IMMUNOELECTRODIFFUSION OF SPECIFIC ANTIBODIES DIRECTED AGAINST THE THREE ANTIGENS FROM WHICH THE RNA AND THE CAPSULAR PS ISSUE | | | | | |
|---|---|---|---|---|---|---|
| | *Streptococcus pneumoniae* Type I (Height of the "Rockets" in mm) | | *Streptococcus pneumoniae* Type II (Height of the "Rockets" in mm) | | *Streptococcus pneumoniae* Type III (Height of the "Rockets" in mm) | |
| Female mice $OF_1$ | Before treatment | After treatment | Before treatment | After treatment | Before treatment | After treatment |
| 1 | 10 | 20 | 9 | 13 | 8 | 15 |
| 2 | 8 | 20 | 8 | 15 | 10 | 15 |
| 3 | 8 | 18 | 0 | 16 | 10 | 14 |
| 4 | 6 | 18 | 0 | 15 | 6 | 12 |
| 5 | 4 | 17 | 4 | 16 | 5 | 16 |
| 6 | 10 | 20 | 12 | 20 | 12 | 18 |
| 7 | 10 | 19 | 0 | 16 | 7 | 14 |
| 8 | 10 | 16 | 7 | 12 | 7 | 16 |
| 9 | 8 | 17 | 7 | 16 | 0 | 12 |

-continued

INVESTIGATION BY IMMUNOELECTRODIFFUSION OF SPECIFIC ANTIBODIES
DIRECTED AGAINST THE THREE ANTIGENS FROM WHICH THE RNA AND
THE CAPSULAR PS ISSUE

| Female mice OF$_1$ | Streptococcus pneumoniae Type I (Height of the "Rockets" in mm) | | Streptococcus pneumoniae Type II (Height of the "Rockets" in mm) | | Streptococcus pneumoniae Type III (Height of the "Rockets" in mm) | |
|---|---|---|---|---|---|---|
|  | Before treatment | After treatment | Before treatment | After treatment | Before treatment | After treatment |
| 10 | 10 | 15 | 7 | 12 | 8 | 16 |

Vaccination procedure using the formulation of Example 2, 5 injection in 2 weeks.
¼ of dose per injection, i.e. 1.25 μg of RNA + 0.05 μg of P.S. of each type per animal.

We claim:

1. A vaccinal complex comprising RNA selected from bacterial ribosomal RNA and fragments of bacterial ribosomal RNA, on which are coupled from 1 to 5% by weight of a specific antigen of bacterial serotype.

2. A complex according to claim 1, wherein the RNA and the specific antigen originate from the same bacterial strains.

3. A complex according to claim 1, wherein the RNA and the specific antigen originate from different bacterial strains.

4. A complex according to claim 1, wherein the specific antigen is selected from the following: Capsular polysaccharides, Membrane lipopolysaccharides of gram-negative bacteria, specific membrane proteins, and teichoic and lipopteichoic acids of gram-negative bacteria.

5. A complex according to claim 4, wherein the specific antigen is selected from capsular polysaccharides of at least one of the following species:
   Klebsiella pneumoniae,
   Streptococcus pneumoniae,
   Hemophilus influenzae, and
   Escherichia coli.

6. A complex according to claim 4, wherein the specific antigen is selected from membrane lipopolysaccharides of at least one of the following species:
   Klebseilla pneumoniae,
   Serratia marcescens,
   Escherichia coli,
   Neisseria meningitidis, and
   Salmonella typhimurium.

7. A complex according to claim 4, wherein the specific antigen is selected from specific membrane proteins of at least one of the following species:
   Escherichia coli,
   Serratia marcescens,
   Salmonella typhimurium, and
   Streptococcus pyogenes.

8. A complex according to claim 4, wherein the specific antigen is selected from teichoic and lipoteichoic acids of at least one of the following genera:
   Streptococci,
   Staphylococci, and
   Lactobacillae.

9. A complex according to claim 1, wherein the ribosomal RNA is extracted from the ribosomes of at least one of the following:
   Streptococcus pneumoniae,
   Streptococcus pyogenes,
   Staphylococcus aureus,
   Klebsiella pneumoniae,
   Serratia marcescens,
   Escherichia coli,
   Salmonella typhimurium,
   Corynebacterium,
   Mycobacterium.

10. A complex according to claim 1, wherein the fragments of bacterial ribosomal RNA have a molecular weight of between $3 \times 10^4$ and $2 \times 10^5$ daltons.

11. A complex according to claim 10, wherein the fragments of bacterial ribosomal RNA have a molecular weight of between 30,000 and 50,000.

12. A complex according to claim 1, wherein coupling is produced by covalent bonds.

13. A vaccine against pathogenic bacteria comprising a pharmaceutically acceptable support and an effective amount of the vaccinal complex of claim 1 to inoculate a patient.

14. A method for inoculating a patent comprising administering to said patient the vaccine of claim 13.

* * * * *